United States Patent
Yamashita et al.

(10) Patent No.: US 9,822,754 B2
(45) Date of Patent: Nov. 21, 2017

(54) FUEL PROPERTY DETERMINATION APPARATUS FOR INTERNAL COMBUSTION ENGINE

(71) Applicant: Toyota Jidosha Kabushiki Kaisha, Toyota-shi (JP)

(72) Inventors: Akitaka Yamashita, Okazaki (JP); Mikio Watanabe, Chiryu (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 159 days.

(21) Appl. No.: 14/813,580

(22) Filed: Jul. 30, 2015

(65) Prior Publication Data

US 2016/0032884 A1 Feb. 4, 2016

(30) Foreign Application Priority Data

Jul. 31, 2014 (JP) ................. 2014-155860

(51) Int. Cl.
*F02P 15/00* (2006.01)
*F01P 3/20* (2006.01)
(Continued)

(52) U.S. Cl.
CPC ............... *F02P 15/006* (2013.01); *F01P 3/20* (2013.01); *F01P 11/16* (2013.01);
(Continued)

(58) Field of Classification Search
CPC ........ F02P 15/006; F02P 5/1506; F02P 9/002; F01P 11/16; F01P 3/20; G01N 33/225;
(Continued)

(56) References Cited

U.S. PATENT DOCUMENTS 5,542,394 A * 8/1996 Tomisawa ............... F02D 41/00
123/491
5,711,272 A * 1/1998 Maegawa ........... F02D 41/0025
123/1 A
(Continued)

FOREIGN PATENT DOCUMENTS

JP 11-241644 9/1999
JP 3863362 12/2006

*Primary Examiner* — Hung Q Nguyen
*Assistant Examiner* — Xiao Mo
(74) *Attorney, Agent, or Firm* — Oblon, McClelland, Maier & Neustadt, L.L.P.

(57) ABSTRACT

A fuel property determination apparatus for an internal combustion engine is applied to an internal combustion engine that is equipped with an ignition plug and an ignition timing controller. An electronic control unit provided in the fuel property determination apparatus executes a determination process of making a determination on a property of a fuel supplied to the internal combustion engine based on an ignition sufficiency ratio, during a predetermined period after startup of the internal combustion engine. The electronic control unit is configured to determine that the property of the fuel is heavy when a determination index value that is obtained by subjecting the ignition sufficiency ratio to a smoothing process is equal to or larger than a predetermined threshold. The electronic control unit is configured to set a smoothing coefficient to a value corresponding to each of a first period, a second period, and a third period.

5 Claims, 7 Drawing Sheets

(51) Int. Cl.

| | | |
|---|---|---|
| *F01P 11/16* | (2006.01) | |
| *F02D 35/00* | (2006.01) | |
| *F02P 9/00* | (2006.01) | |
| *G01N 33/22* | (2006.01) | |
| *F02P 5/15* | (2006.01) | |
| *F02D 41/00* | (2006.01) | |
| *F02D 41/06* | (2006.01) | |

(52) U.S. Cl.
CPC ..... *F02D 35/0007* (2013.01); *F02D 41/0025* (2013.01); *F02P 5/1506* (2013.01); *F02P 9/002* (2013.01); *G01N 33/225* (2013.01); *F02D 41/06* (2013.01); *F02D 41/068* (2013.01); *F02D 2200/0612* (2013.01); *Y02T 10/46* (2013.01)

(58) Field of Classification Search
CPC . Y02T 10/46; F02D 2200/0612; F02D 41/06; F02D 41/068; F02D 41/0025; F02D 35/0007
See application file for complete search history.

(56) References Cited

U.S. PATENT DOCUMENTS

| | | | | |
|---|---|---|---|---|
| 2005/0065710 A1* | 3/2005 | Yasuda | .................. | F02D 33/003 701/114 |
| 2008/0154485 A1* | 6/2008 | Yasuda | ................... | F01N 3/101 701/113 |
| 2008/0162017 A1* | 7/2008 | Nagata | .................... | F02D 35/02 701/103 |

\* cited by examiner

FUEL PROPERTY DETERMINATION APPARATUS FOR INTERNAL COMBUSTION ENGINE

INCORPORATION BY REFERENCE

The disclosure of Japanese Patent Application No. 2014-155860 filed on Jul. 31, 2014 including the specification, drawings and abstract is incorporated herein by reference in its entirety.

BACKGROUND OF THE INVENTION

1. Field of the Invention

The invention relates to a fuel property determination apparatus for an internal combustion engine. More specifically, the invention relates to a fuel property determination apparatus for an internal combustion engine that makes it possible to more accurately determine, even at low temperatures, whether or not the fuel supplied to the internal combustion engine is heavy fuel.

2. Description of Related Art

In the relevant technical field, it is known that the property of the fuel supplied to the internal combustion engine has an influence on the control of an air-fuel ratio and the like in the internal combustion engine. For example, the volatility of heavy fuel is lower than the volatility of standard fuel. Therefore, when the control adapted for standard fuel is executed, the operability of the internal combustion engine and/or the exhaust emission properties may deteriorate. Thus, in the relevant technical field, various attempts to make a determination on the property of fuel have been made with a view to executing the control corresponding to the property of fuel.

For example, in an internal combustion engine that is equipped with an ignition timing controller that executes feedback control of an ignition timing such that the rotational speed of the internal combustion engine converges to a target rotational speed at the time of idling after startup, it is proposed to calculate an ignition timing correction amount at the time when the engine rotational speed stabilizes with respect to the target rotational speed and an ignition timing correction amount that converges after stabilization of the rotational speed, and to make a determination on the property of fuel based on a difference between those ignition timing correction amounts (e.g., see U.S. Pat. No. 3,863,362).

Besides, it is also known to make a more accurate determination on the property of fuel based on a ratio of a correction amount from a basic ignition timing corresponding to a target rotational speed (which will be referred to hereinafter as "an ignition timing correction amount" in some cases) to an allowable range of an ignition timing that is determined in accordance with the target rotational speed, a temperature and the like of an internal combustion engine (which will be referred to hereinafter as "a maximum ignition correction width" in some cases).

As described previously, in the relevant technical field, various attempts to make a determination on the property of fuel have been made with a view to executing the control corresponding to the property of fuel. It is also known to make a more accurate determination on the property of fuel based on the ratio of the ignition timing correction amount to the maximum ignition correction width. Thus, the air-fuel ratio and the like can be controlled in accordance with the property of fuel, and the operability of the internal combustion engine and/or the exhaust emission properties can be held good.

However, the rotational speed tends to greatly fluctuate immediately after startup of the internal combustion engine, for example, in a cold land. In this case, the ignition timing correction amount greatly fluctuates as well. Therefore, with a method of making a determination on the property of fuel according to the related art as described above, it may be erroneously determined that heavy fuel is used despite the use of standard fuel. This problem tends to manifest itself as the use of automobiles becomes widespread all over the world these days.

SUMMARY OF THE INVENTION (US, DE, CN, RU)

The invention has been made in view of the aforementioned problem. That is, the invention provides "a fuel property determination apparatus for an internal combustion engine (which will be referred to hereinafter as "the apparatus according to the invention" in some cases)" that makes it possible to more accurately determine, even at low temperatures, whether or not the fuel supplied to the internal combustion engine is heavy fuel.

The fuel property determination apparatus for an internal combustion engine, which is equipped with an ignition plug having a spark generation portion, includes an electronic control unit.

The electronic control unit is configured to (i) correct an ignition timing as a timing for generating a spark from the spark generation portion, (ii) execute feedback control of an engine rotational speed such that an engine rotational speed converges to a target rotational speed, (iii) calculate an ignition sufficiency ratio during a preset period after startup of the internal combustion engine, and execute a determination process of making a determination on a property of a fuel supplied to the internal combustion engine based on the ignition sufficiency ratio, the ignition sufficiency ratio being a ratio of an advancement correction amount of the ignition timing to a maximum ignition correction width as a maximum width that allows the ignition timing to be corrected when the ignition timing is corrected in the feedback control, (iv) determine that the property of the fuel is heavy when a determination index value obtained by subjecting the ignition sufficiency ratio to a smoothing process is equal to or larger than a predetermined threshold, the smoothing process being a process of calculating a weighted average of an ignition sufficiency ratio obtained this time and a determination index value obtained last time, and (v) set a smoothing coefficient to a value corresponding to each of a first period, a second period, and a third period, the smoothing coefficient being an inverse of a coefficient corresponding to a weight of the ignition sufficiency ratio obtained this time in the smoothing process, the first period being a period from startup of the internal combustion engine to attainment of the target rotational speed by the engine rotational speed, the second period being a period from attainment of the target rotational speed by the engine rotational speed to lapse of a predetermined period, and the third period being a period after lapse of the predetermined period from attainment of the target rotational speed by the engine rotational speed.

Besides, in the apparatus according to the invention, it may be possible that a first smoothing coefficient is larger than a third smoothing coefficient, and the third smoothing coefficient is larger than or equal to a second smoothing coefficient. It should be noted herein that the first smoothing coefficient is a smoothing coefficient in the first period, that the second smoothing coefficient is a smoothing coefficient in the second period, and that the third smoothing coefficient is a smoothing coefficient in the third period.

Besides, in the apparatus according to the invention, the electronic control unit may be configured to determine that the property of the fuel is heavy when the engine rotational speed has not reached the target rotational speed even after lapse of a predetermined period t1 from startup of the internal combustion engine.

Besides, the fuel property determination apparatus may further includes a coolant temperature sensor configured to detect a temperature of a coolant in the internal combustion engine. The electronic control unit may be configured to set the third smoothing coefficient to 1 when the temperature of the coolant detected by the coolant temperature sensor at a time of startup of the internal combustion engine is equal to or higher than a predetermined threshold TL.

Besides, the fuel property determination apparatus may further includes a fuel feed detector configured to detect an operation of feeding fuel. The electronic control unit may be configured to, when the fuel feed detector detects the operation of feeding fuel, (i) nullify a result of determination obtained by the determination process, and (ii) prohibit the determination process from being executed when the electronic control unit has determined that the property of the fuel supplied to the internal combustion engine is heavy.

In the fuel property determination apparatus according to the invention as described above, a determination on the property of fuel is made based on the determination index value that is obtained by subjecting the aforementioned ignition sufficiency ratio to "the smoothing process" in which "the smoothing coefficient" corresponding to each of the aforementioned three periods is used. As a result, the ignition sufficiency ratio (i.e., the determination index value) appropriately corrected by "the smoothing process" does not reach a threshold Ch. That is, the possibility of an erroneous determination that the property of fuel is "heavy" despite the use of standard fuel is reduced.

As described above, the fuel property determination apparatus for the internal combustion engine according to the invention classifies the predetermined period after startup of the internal combustion engine in accordance with the fluctuation pattern of the engine rotational speed, and determines that the property of fuel is "heavy" when the determination index value obtained by subjecting the ignition sufficiency ratio to "the smoothing process" corresponding to each of the periods is equal to or larger than the predetermined threshold Ch. As a result, the apparatus according to the invention makes it possible to more accurately determine, even at low temperatures, whether or not the fuel supplied to the internal combustion engine is heavy fuel.

Other objects, other features, and accompanying advantages of the invention will be easily understood from the description of respective embodiments of the invention that will be described with reference to the following drawings.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Figure 1:
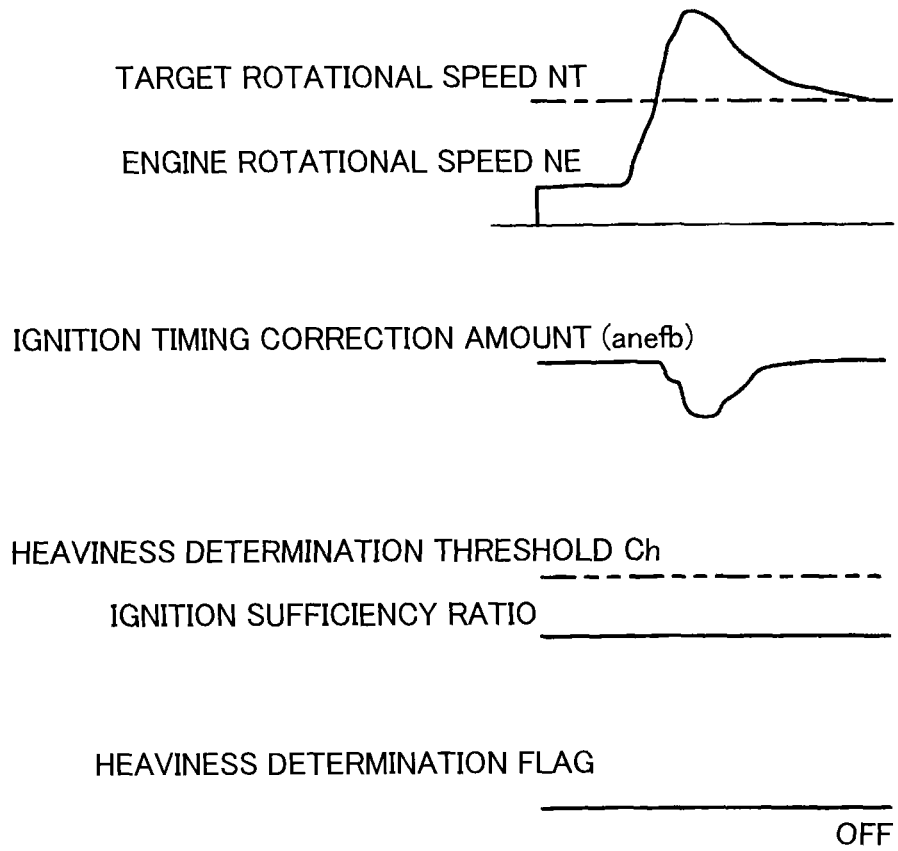
FIG. 1 is a schematic time chart showing changes in an engine rotational speed, an ignition timing correction amount, an ignition sufficiency ratio, and a heaviness determination flag indicating "that fuel is heavy" in a predetermined period after startup of an internal combustion engine that uses standard fuel at room temperatures.

"A fuel property determination apparatus for an internal combustion engine (which will be referred to hereinafter as "the determination apparatus" in some cases) according to each of embodiments of the invention will be described hereinafter with reference to the accompanying drawings.

First of all, the first embodiment of the invention will be described. The determination apparatus according to the first embodiment of the invention (which will be referred to hereinafter simply as "the first apparatus") is applied to an internal combustion engine that is equipped with an ignition plug that has a spark generation portion, and an ignition timing controller that corrects an ignition timing as a timing for generating a spark from the spark generation portion, and that executes feedback control of an engine rotational speed such that the engine rotational speed converges to a target rotational speed. The fuel property determination apparatus for this internal combustion engine calculates an ignition sufficiency ratio, which is a ratio of an advancement correction amount of the ignition timing to a maximum ignition correction width as "a maximum width that allows the ignition timing to be corrected" when the ignition timing is corrected in the feedback control, during a predetermined period after startup of the internal combustion engine. The fuel property determination apparatus is equipped with a control unit that executes a determination process of making a determination on a property of a fuel supplied to the internal combustion engine based on this ignition sufficiency ratio. The control unit determines that the property of the fuel is "heavy" when a determination index value that is obtained by subjecting the ignition sufficiency ratio to "a smoothing process" is equal to or larger than a predetermined threshold Ch. "The smoothing process" is a process of calculating a weighted average of an ignition sufficiency ratio obtained this time and a determination index value obtained last time. The control unit sets "a smoothing coefficient" to a value corresponding to each of a first period, a second period, and a third period. The smoothing coefficient is an inverse of a coefficient corresponding to a weight of the ignition sufficiency ratio obtained this time in "the smoothing process". The first period is a period from startup of the internal combustion engine to attainment of the target rotational speed by the engine rotational speed. The second period is a period from attainment of the target rotational speed by the engine rotational speed to the lapse of a predetermined period t2. Then, the third period is a period after the lapse of the predetermined period t2 from attainment of the target rotational speed by the engine rotational speed.

As described previously, the maximum ignition correction width is an allowable range of the ignition timing that is determined in accordance with the target rotational speed, temperature and the like of the internal combustion engine at each moment. In other words, the maximum ignition correction width is a range of the ignition timing that is determined by a difference between a most advanced ignition timing absef and a most retarded ignition timing aopmn and that makes it possible to achieve stable idling operation at the target rotational speed, temperature and the like of the internal combustion engine at each moment. Besides, as described above, the ignition sufficiency ratio is a ratio of the advancement correction amount of the ignition timing to the maximum ignition correction width. In other words, the ignition sufficiency ratio is a ratio of a correction amount of the ignition timing toward the advancement side to a variable range of the ignition timing. Accordingly, when the ignition timing is corrected toward the retardation side, the ignition sufficiency ratio is "0 (zero)".

As described previously, it is conventionally known to make a determination on the property of fuel based on "the ratio of the ignition timing correction amount to the maximum ignition correction width" such as the aforementioned ignition sufficiency ratio. However, immediately after cold startup of the internal combustion engine, the rotational speed greatly fluctuates, and the ignition timing correction amount greatly fluctuates, too. Therefore, in some cases, it is erroneously determined that standard fuel is heavy fuel.

Figure 2:
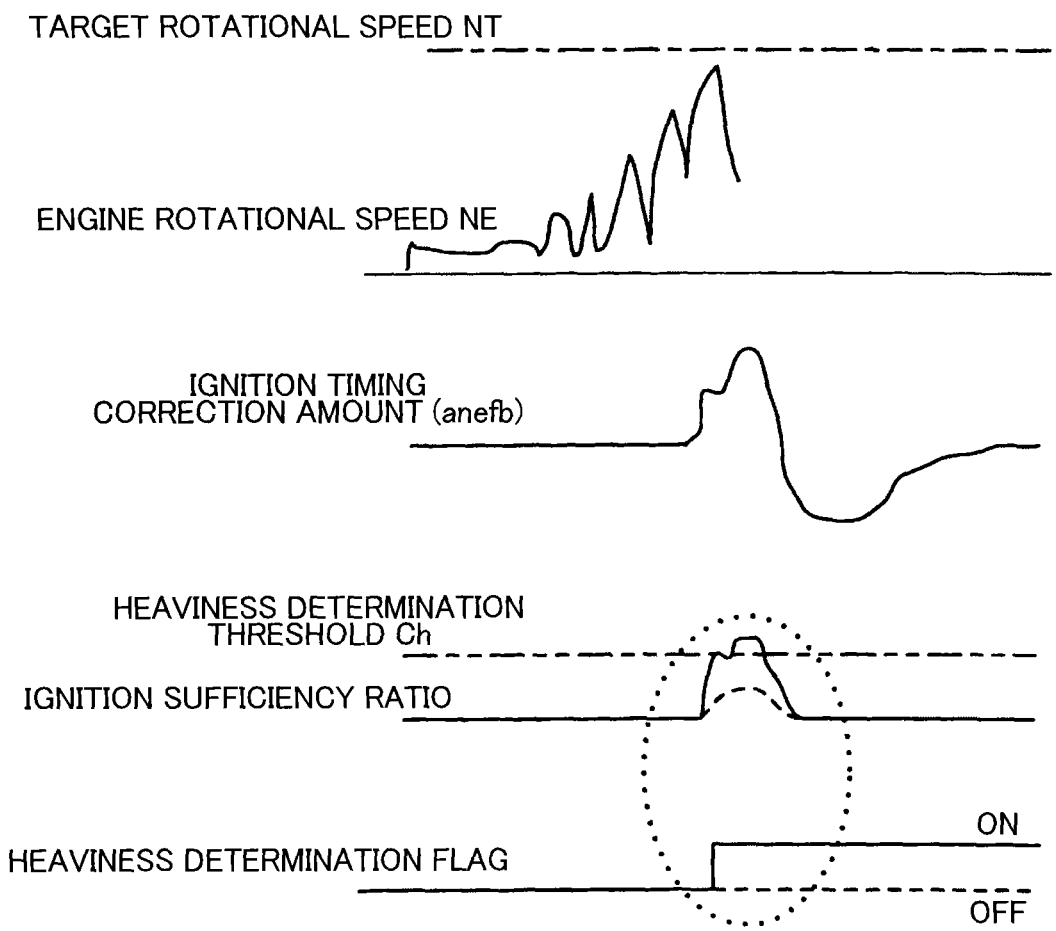
FIG. 2 is a schematic time chart showing changes in the engine rotational speed, the ignition timing correction amount, the ignition sufficiency ratio, and the heaviness determination flag indicating "that fuel is heavy" in a predetermined period after startup of an internal combustion engine that uses standard fuel at low temperatures.

The aforementioned erroneous determination will now be described hereinafter in detail with reference to the accompanying drawings. FIG. 1 is a schematic time chart showing changes in an engine rotational speed NE, an ignition timing correction amount (anefb), an ignition sufficiency ratio (anefbrte), and a heaviness determination flag as a flag indicating "that fuel is heavy" in a predetermined period after startup of an internal combustion engine that uses standard fuel at room temperatures. FIG. 2 is a schematic time chart showing the aforementioned changes in a predetermined period after startup of an internal combustion engine that uses standard fuel at low temperatures.

As shown in FIG. 1, in the internal combustion engine that uses standard fuel at room temperatures, the engine rotational speed NE swiftly rises after startup, and exceeds a target rotational speed NT (indicated by an alternate long and short dash line). Thus, the ignition timing is corrected to be retarded through the aforementioned feedback control, and the engine rotational speed NE starts falling. As the engine rotational speed NE falls, the retardation correction amount of the ignition timing is reduced, and the engine rotational speed NE soon converges to the target rotational speed NT. In the meantime, the ignition timing is not corrected to be advanced, so the ignition sufficiency ratio remains equal to "0 (zero)". Accordingly, the ignition sufficiency ratio does not rise to or above a heaviness determination threshold Ch as a threshold for determining "that fuel is heavy". As a result, the heaviness determination flag is held OFF.

On the other hand, as shown in FIG. 2, even in the internal combustion engine that uses standard fuel, the engine rotational speed NE does not swiftly rise after startup at low temperatures. The engine rotational speed NE gradually rises while repeatedly rising and falling, but is unlikely to reach the target rotational speed NT (indicated by the alternate long and short dash line). After that, when feedback control is started, the ignition timing is corrected to be advanced, and the engine rotational speed NE finally exceeds the target rotational speed NT. Thus, the ignition timing is corrected to be retarded, and the engine rotational speed NE starts falling. As the engine rotational speed NE falls, the retardation correction amount of the ignition timing is reduced, and the engine rotational speed NE soon converges to the target rotational speed NT. In an example shown in FIG. 2, as indicated by a region surrounded by a dotted ellipse, the ignition sufficiency ratio rises to and above the heaviness determination threshold Ch (as indicated by a solid line). As a result, the heaviness determination flag is turned ON. That is, in this case, it is erroneously determined that heavy fuel has been used despite the use of standard fuel.

As described above, at low temperatures, the rotational speed greatly fluctuates immediately after startup of the internal combustion engine, and the ignition timing correction amount greatly fluctuates, too. Therefore, in some cases, it is erroneously determined that heavy fuel is used despite the use of standard fuel. As a result of conducting strenuous studies with a view to reducing the possibility of such an erroneous determination, the inventor has found out that it is possible to accurately determine, even at low temperatures, whether or not the fuel supplied to the internal combustion engine is heavy fuel, by making a determination on the property of fuel based on a determination index value that is obtained by subjecting the ignition sufficiency ratio to "the smoothing process". Incidentally, the control unit with which the apparatus according to the invention is equipped determines that the property of fuel is "heavy" when the determination index value obtained by subjecting the ignition sufficiency ratio to "the smoothing process" is equal to or larger than a predetermined threshold (the heaviness determination threshold Ch).

In FIG. 2, the ignition sufficiency ratio subjected to the aforementioned "smoothing process" (i.e., the determination index value) is indicated by a broken curve. The determination index value is smaller than the ignition sufficiency ratio due to "the smoothing process", and hence does not reach the heaviness determination threshold Ch. Accordingly, the possibility of an erroneous determination as described above can be reduced by making a determination on the property of fuel using the determination index value instead of the ignition sufficiency ratio. In this manner, the determination index value is made sufficiently small by subjecting the ignition sufficiency ratio to "the smoothing process". It is important to execute "the smoothing process" to such an extent that a correct determination is made on the property of fuel.

Figure 3:
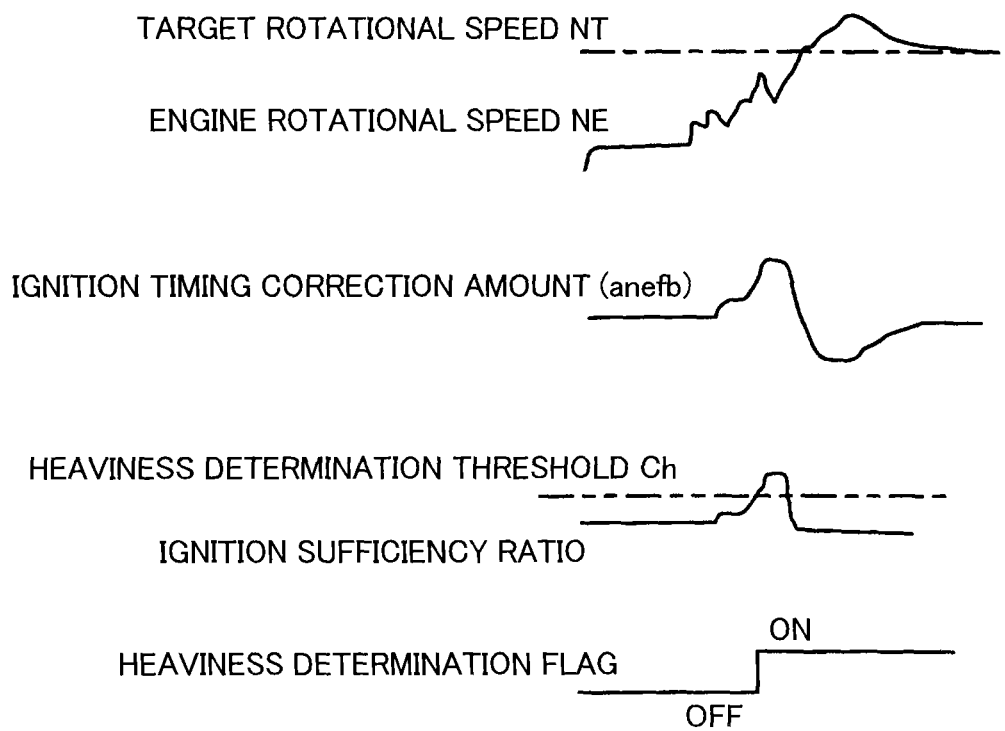
FIG. 3 is a schematic time chart showing changes in the engine rotational speed, the ignition timing correction amount, the ignition sufficiency ratio, and the heaviness determination flag indicating "that fuel is heavy" in a predetermined period after startup of an internal combustion engine that uses heavy fuel at room temperatures.
Figure 4:
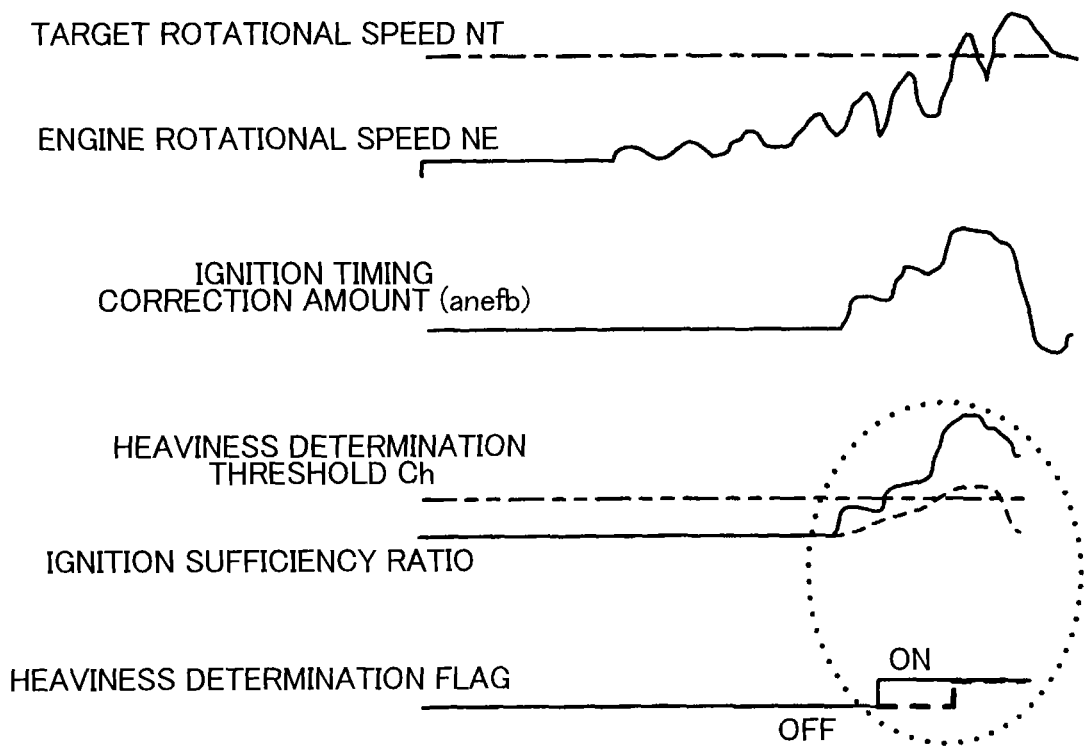
FIG. 4 is a schematic time chart showing changes in the engine rotational speed, the ignition timing correction amount, the ignition sufficiency ratio, and the heaviness determination flag indicating "that fuel is heavy" in a predetermined period after startup of an internal combustion engine that uses heavy fuel at low temperatures.

Incidentally, FIGS. 3 and 4 are schematic time charts similar to FIGS. 1 and 2 in the case where heavy fuel is used.

FIG. 3 shows changes in the engine rotational speed NE, the ignition timing correction amount (anefb), the ignition sufficiency ratio (anefbrte), and the heaviness determination flag in a predetermined period after startup of an internal combustion engine that uses heavy fuel at room temperatures. FIG. 4 shows the aforementioned changes at low temperatures.

As shown in FIG. 3, in the internal combustion engine that uses heavy fuel, even at room temperatures, the engine rotational speed NE does not swiftly rise after startup, and is unlikely to reach the target rotational speed NT (indicated by the alternate long and short dash line). As a result, the heaviness determination flag is turned ON as soon as the ignition sufficiency ratio rises to or above the heaviness determination threshold Ch. On the other hand, as shown in FIG. 4, at low temperatures, the speed at which the engine rotational speed NE rises further decreases, and the attainment of the target rotational speed NT by the engine rotational speed NE is further retarded. As a result, the advancement correction amount of the ignition timing further increases, and the ignition sufficiency ratio rises to and above the heaviness determination threshold Ch (as indicated by a solid line) as indicated by a region surrounded by a dotted ellipse. Accordingly, in this case as well, the heaviness determination flag is turned ON.

Incidentally, in the example shown in FIG. 4, the determination index value (indicated by a broken line) as the ignition sufficiency ratio subjected to "the smoothing process" also rises to and above the heaviness determination threshold Ch, although it is slower than the ignition sufficiency ratio (indicated by a solid line). That is, through a determination based on the determination index value as well, it is correctly determined that the property of fuel is "heavy", and the heaviness determination flag is turned ON. In this manner, the determination index value does not become too small even when the ignition sufficiency ratio is subjected to "the smoothing process", and it is also important to execute "the smoothing process" to such an extent that a correct determination is made on the property of fuel.

Incidentally, "the smoothing process" refers to a process of updating existing data by smoothing changes from the exiting data to latest data (reducing the degree of reflection), instead of completely replacing the existing data with the latest data by directly reflecting changes from the existing data to the latest data (with the degree of reflection of the latest data being 100%). In the apparatus according to the invention, "the smoothing process" is a process of calculating a weighted average of an ignition sufficiency ratio obtained this time and a determination index value obtained last time. For example, "the smoothing process" can be expressed by a formula (1) shown below.

[Formula 1]

$$M_n = \alpha R_n + (1-\alpha)M_{n-1} = (1/\beta) \times R_n + (1-1/\beta)M_{n-1} = M_{n-1} + (R_n - M_{n-1})/\beta \quad (1)$$

In the aforementioned formula, $M_n$ represents the current (the n-th) determination index value, $M_{n-1}$ represents the last (the (n−1)-th) determination index value, $R_n$ represents the current (the n-th) ignition sufficiency ratio, $\alpha$ represents the weight of $R_n$, and $\beta$ represents the inverse of $\alpha$. As is apparent from the aforementioned formula, as $\beta$ increases (as $\alpha$ decreases), the degree of reflection of $R_n$ as the latest data decreases, and the degree of "the smoothing process" in calculating $M_n$ increases. In the present specification, this value $\beta$ is defined as "the smoothing coefficient".

By the way, the inventor has found out that the fluctuation pattern of the engine rotational speed NE changes as time passes after startup of the internal combustion engine. Accordingly, in order to execute "the smoothing process" to an appropriate extent as described above, it is desirable to determine the degree of "the smoothing process" (i.e., the magnitude of "the smoothing coefficient") in accordance with the lapse of time after startup of the internal combustion engine. Thus, the control unit with which the apparatus according to the invention is equipped classifies the period after startup of the internal combustion engine into three periods that will be enumerated below, and sets "the smoothing coefficient" in accordance with each of the periods.

The first period is a period from startup of the internal combustion engine to attainment of the target rotational speed by the engine rotational speed. The second period is a period from attainment of the target rotational speed by the engine rotational speed to the lapse of the predetermined period t2. The third period is a period after the lapse of the aforementioned predetermined period t2 after attainment of the target rotational speed by the engine rotational speed.

Figure 5:
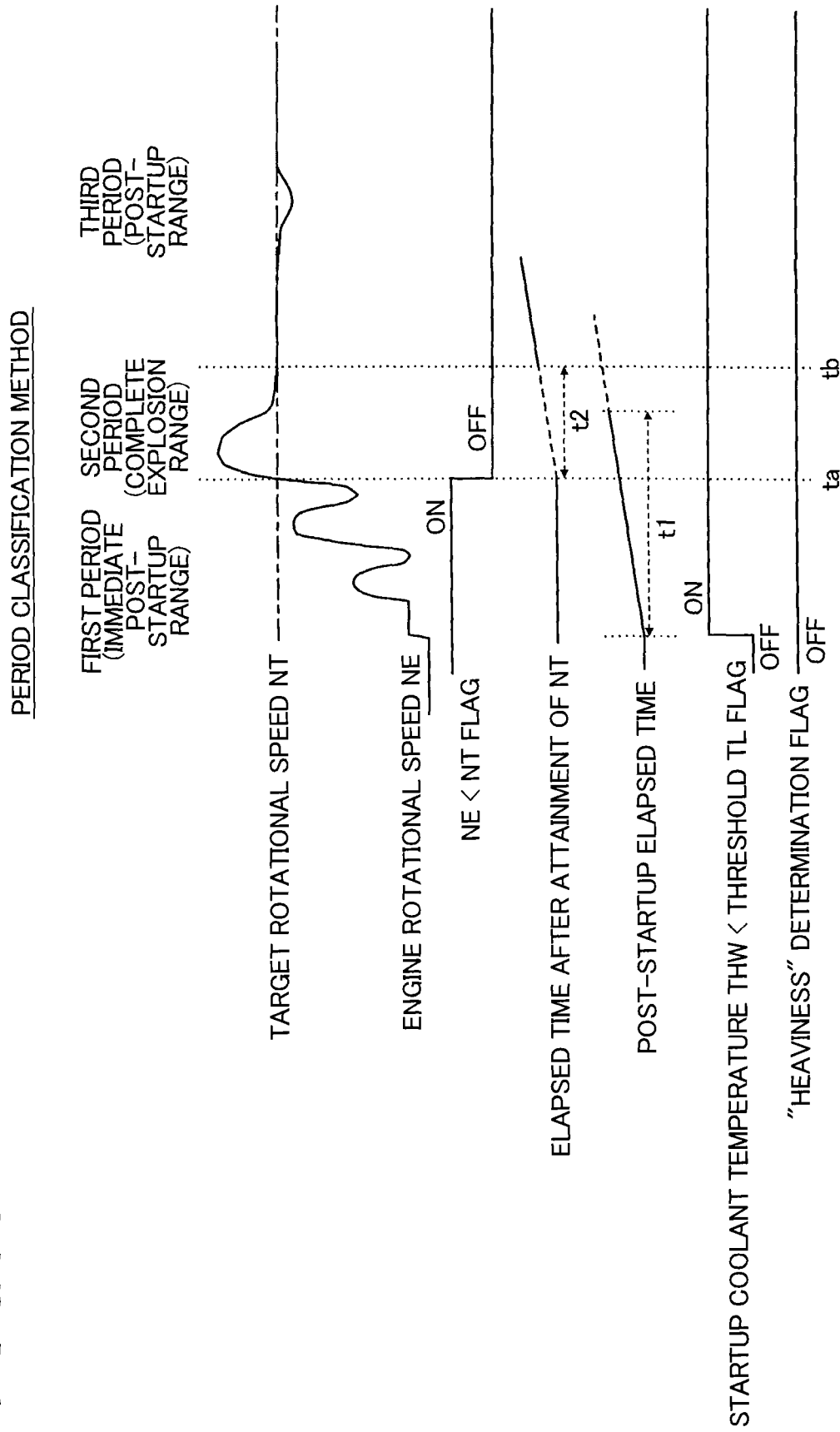
FIG. 5 is a schematic time chart illustrating a method of classifying the predetermined period after startup of the internal combustion engine in accordance with a fluctuation pattern of the engine rotational speed.

A method of classifying the aforementioned period will now be described hereinafter in detail with reference to the accompanying drawings. As indicated by a curve shown in an upper part of FIG. 5, the engine rotational speed NE is not stable immediately after startup of the internal combustion engine, and gradually approaches the target rotational speed NT while repeatedly rising and falling. In due course at a time ta, the engine rotational speed NE reaches the target rotational speed NT. At this time, "an NE<NT flag" indicating that the engine rotational speed NE has not reached the target rotational speed NT is turned OFF from its ON state. This period from startup of the internal combustion engine to the time ta (an immediate post-startup range) is classified as "the first period". In this first period, the engine rotational speed NE greatly fluctuates as described above.

After that, the engine rotational speed NE rises above the target rotational speed NT, and then converges soon to the target rotational speed NT at a time tb through feedback control by the aforementioned ignition timing controller. A period from the time ta when the engine rotational speed NE reaches the target rotational speed NT to the time tb when the engine rotational speed NE converges to the target rotational speed NT (a complete explosion range) is classified as "the second period". Incidentally, the length (t2) of the period from the time ta to the time tb can be empirically specified based on, for example, an experiment or the like using the internal combustion engine. Accordingly, the second period can be determined as a period from attainment of the target rotational speed NT by the engine rotational speed NE to the lapse of the predetermined period t2. In this second period, the engine rotational speed NE converges toward the target rotational speed NT as described above, and does not greatly fluctuate.

As described above, the subsequent third period is a period after the lapse of the aforementioned predetermined period t2 from attainment of the target rotational speed NT by the engine rotational speed NE (a post-startup range). In this third period, the engine rotational speed NE is stable, and is estimated not to fluctuate greatly. In fact, however, the engine rotational speed NE and/or the target rotational speed NT may change due to an external factor, for example, the turning on of an air-conditioner, an operation of shifting from an N (neutral) range to a D (drive) range by a driver of the vehicle, or the like. Incidentally, in FIG. 5, a range in which the engine rotational speed NE (indicated by a solid line) is lower than the target rotational speed NT (indicated by an alternate long and short dash line) due to this external factor (e.g., the turning on of the air-conditioner) is depicted in the third period.

As described above, the fluctuation patterns of the engine rotational speed NE that are assumed in the aforementioned respective three periods are different from one another. Thus, the control unit with which the apparatus according to the invention is equipped sets "the smoothing coefficient" in accordance with (the fluctuation pattern of the engine rotational speed NE assumed in) each of the aforementioned three periods. Thus, the apparatus according to the invention can suitably make a determination on the property of fuel. Incidentally, the concrete value of "the smoothing coefficient" can be appropriately determined in accordance with, for example, the characteristic and the like of the internal combustion engine to which the method according to the invention is applied (the details will be described later).

Figure 6:
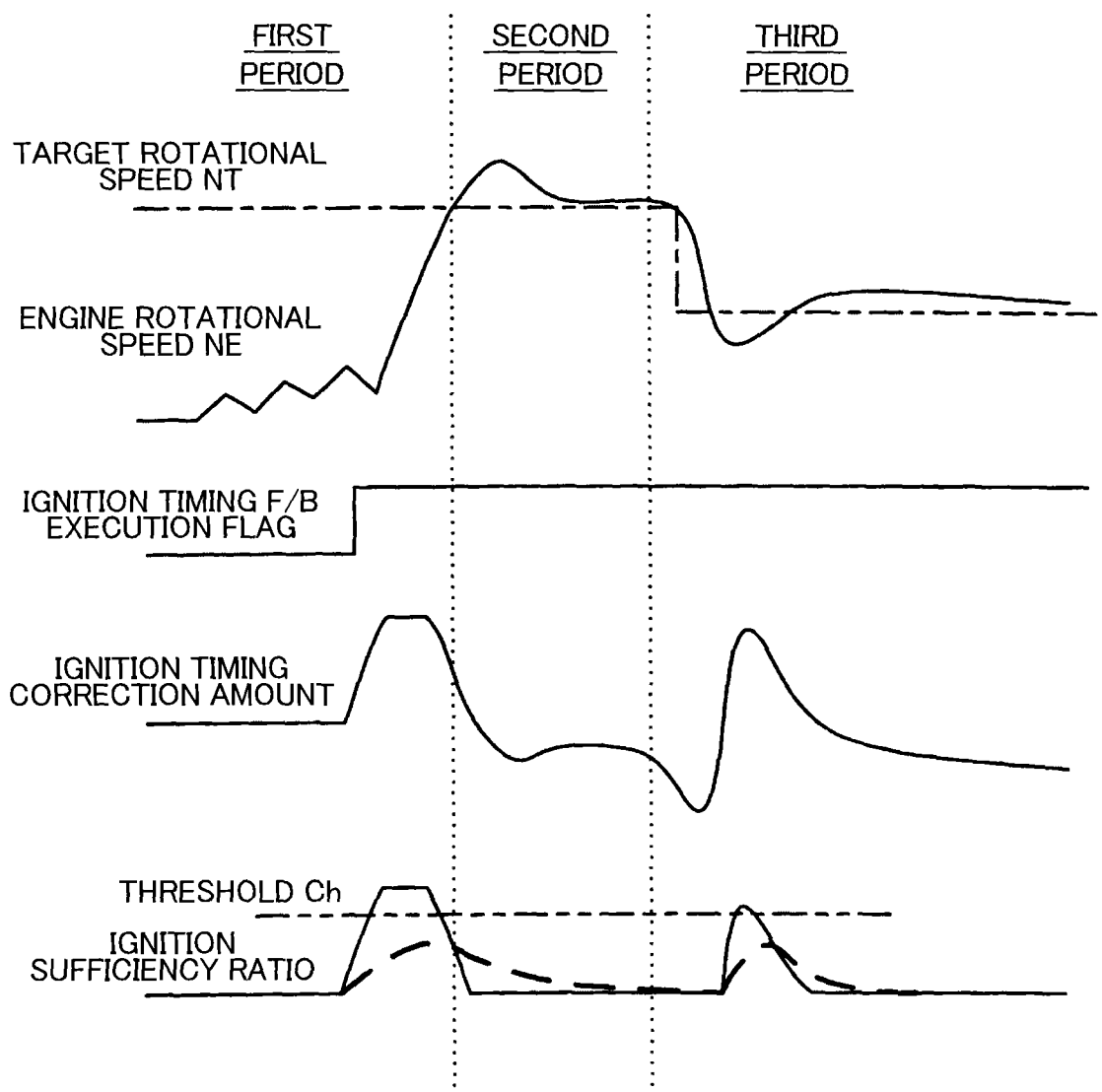
FIG. 6 is a schematic time chart illustrating a method of "a smoothing process" of the ignition sufficiency ratio in the predetermined period after startup of the internal combustion engine, which has been classified in accordance with the fluctuation pattern of the engine rotational speed.

The foregoing will now be described in detail with reference to the accompanying drawings. FIG. 6 is a schematic time chart illustrating a method of "the smoothing process" of the ignition sufficiency ratio in a predetermined period after startup of the internal combustion engine, which has been classified in accordance with the fluctuation pattern of the engine rotational speed. The time chart shown in FIG. 6 indicates fluctuations in the engine rotational speed NE of an internal combustion engine that uses standard fuel in a predetermined period immediately after cold startup, and resultant changes in the ignition timing correction amount and the ignition sufficiency ratio, and the like.

First of all, a conventional art for making a determination on the property of fuel based on the ignition sufficiency ratio will be described. In the first period from startup of the internal combustion engine to attainment of the target rotational speed NT by the engine rotational speed NE (the immediate post-startup range), the engine rotational speed NE greatly fluctuates, and is unlikely to reach the target rotational speed NT. Therefore, as soon as ignition timing feedback control is started (an ignition timing F/B execution flag is turned ON), the ignition timing is drastically corrected to be advanced (the ignition timing correction amount is increased), and the ignition sufficiency ratio increases to become equal to or larger than the threshold Ch. That is, it is erroneously determined that the property of fuel is "heavy" despite the use of standard fuel.

Subsequently, in the second period from attainment of the target rotational speed NT by the engine rotational speed NE to the lapse of the predetermined period t2 (the complete explosion range), the engine rotational speed NE is stable and does not greatly fluctuate. Therefore, the ignition timing correction amount is also stably held at a small value, and the ignition sufficiency ratio does not reach the threshold Ch either. That is, in this period, it is not erroneously determined that the property of fuel is "heavy".

After that, according to this example, in the third period after the lapse of the aforementioned predetermined period t2 from attainment of the target rotational speed NT by the engine rotational speed NE (the post-startup range), the engine rotational speed NE and the target rotational speed NT greatly fall due to an operation of shifting from the N (neutral) range to the D (drive) range by the driver of the vehicle. As a result, the ignition timing correction amount greatly fluctuates, and the ignition sufficiency ratio reaches a level equal to or higher than the threshold Ch. That is, in this case as well, it is erroneously determined that the property of fuel is "heavy" despite the use of standard fuel. Thus, as indicated by a thick broken curve depicted so as to overlap with a curve indicating changes in the ignition sufficiency ratio in FIG. 6, the fuel property determination apparatus for the internal combustion engine according to the present embodiment of the invention reduces the possibility of an erroneous determination that the property of fuel is "heavy". The fuel property determination apparatus for the internal combustion engine according to the invention will be described hereinafter concretely.

Figure 7:
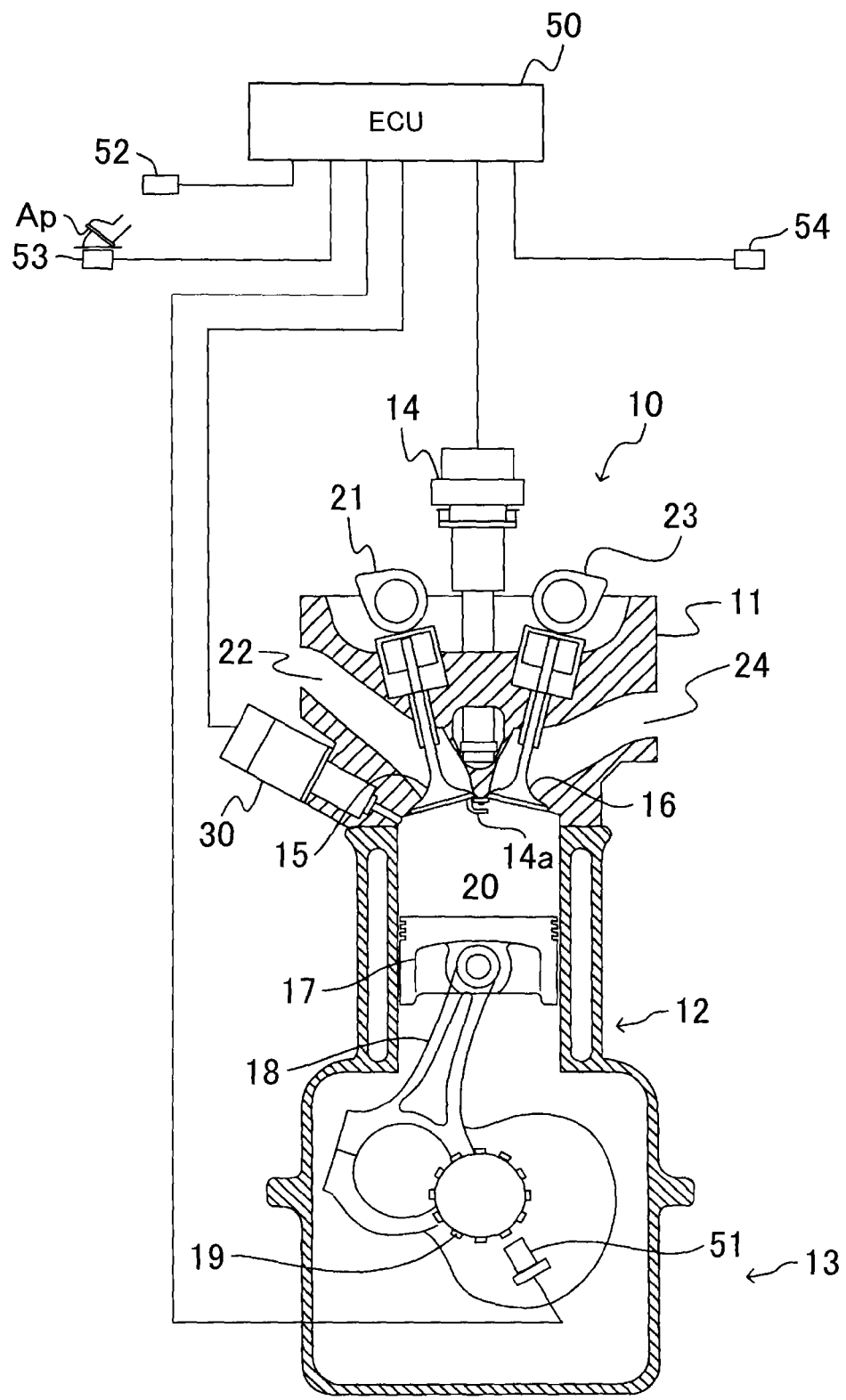
FIG. 7 is a schematic view showing an internal combustion engine to which a fuel property determination apparatus for an internal combustion engine according to the first embodiment of the invention (a first apparatus) is applied.

First of all, the configuration of the internal combustion engine will be described. The first apparatus is applied to an internal combustion engine that is equipped with an ignition plug that has a spark generation portion, and an ignition timing controller that corrects an ignition timing as a timing for generating a spark from the spark generation portion, and that executes feedback control of an engine rotational speed such that the engine rotational speed converges to a target rotational speed. More specifically, the first apparatus is applied to an internal combustion engine (which will be referred to hereinafter as "the engine") 10 shown in FIG. 7.

The engine 10 is a well-known gasoline fuel spark ignition engine. The engine 10 is equipped with a cylinder head 11, a cylinder block 12, a crankcase 13, an ignition device 14 including an ignition plug, an intake valve 15, an exhaust valve 16, a piston 17, a connecting rod 18, a crankshaft 19, and the like. A combustion chamber 20 is formed by a lower wall surface of the cylinder head 11, a wall surface of a cylinder bore that is formed in the cylinder block 12, and a top surface of the piston 17.

The ignition device 14 is disposed in the cylinder head 11 such that a spark generation portion 14a of the ignition plug is exposed to a central portion of an upper surface of the combustion chamber 20. The intake valve 15 is disposed in the cylinder head 11 in such a manner as to open/close "a communication portion between the combustion chamber 20 and an intake port 22 that is formed in the cylinder head 11" by being driven by an intake cam 21. The exhaust valve 16 is disposed in the cylinder head 11 in such a manner as to open/close "a communication portion between the combustion chamber 20 and an exhaust port 24 that is formed in the cylinder head 11" by being driven by an exhaust cam 23. Furthermore, the engine 10 is equipped with a fuel injection valve (an in-cylinder injection valve) 30. The fuel injection valve 30 is disposed in "a region between the intake port 22 and the cylinder block 12" in the cylinder head 11 so as to inject fuel into the combustion chamber 20.

Incidentally, as described above, the engine 10 shown in FIG. 7 is a so-called "side injection internal combustion engine" in which the fuel injection valve 30 that is disposed in the region between the intake port of the cylinder head and the cylinder block injects fuel toward a central axis of the cylinder. However, the first apparatus is applicable not only to this "side injection internal combustion engine" but also to, for example, a so-called "center injection internal combustion engine" in which fuel is injected from a fuel injection valve that is disposed in the vicinity of a central portion of a cylinder head toward a top surface of a piston. Furthermore, the first apparatus is applicable not only to this "in-cylinder injection internal combustion engine" but also to, for example, a so-called "port injection internal combustion engine" in which fuel is injected from a fuel injection valve that is disposed in an intake port of a cylinder head.

Furthermore, the engine 10 is equipped with an ignition timing controller that corrects the ignition timing as a timing for generating a spark from the spark generation portion 14a, and that executes feedback control of the engine rotational speed NE such that the engine rotational speed NE converges to the target rotational speed NT. In the engine 10, an electronic control unit (an ECU) 50 that will be described below functions as the ignition timing controller.

Next, the configuration of the ECU will be described. The ECU 50 is a well-known microcomputer that includes a CPU, a ROM, a RAM, a backup RAM, and the like. The ECU 50 is electrically connected to the ignition device 14, the fuel injection valve 30, and the like, and sends drive signals thereto. In addition, the ECU 50 is electrically connected to a crank position sensor 51, an airflow meter 52, an accelerator pedal depression amount sensor 53, an air-fuel ratio sensor 54, and the like, and receives signals therefrom.

The crank position sensor 51 generates a signal in accordance with a rotational position of the crankshaft 19. The ECU 50 calculates the engine rotational speed NE based on a signal from the crank position sensor 51. Furthermore, the ECU 50 acquires an absolute crank angle with respect to, for example, a compression top dead center in one of cylinders, based on signals from the crank position sensor 51 and a cam position sensor (not shown). The airflow meter 52 generates a signal indicating a flow rate of intake air in the engine 10. The accelerator pedal depression amount sensor 53 generates a signal indicating a depression amount of an accelerator pedal Ap. The air-fuel ratio sensor 54 generates a signal indicating an air-fuel ratio of exhaust gas.

Next, the configuration and operation of the first apparatus will be described. In the first apparatus, the ECU 50 with which the engine 10 is equipped functions as the control unit. This control unit calculates an ignition sufficiency ratio, which is a ratio of an advancement correction amount of the ignition timing to a maximum ignition correction width as "a maximum width that allows the ignition timing to be corrected" when the ignition timing is corrected in feedback control by the ignition timing controller, during a predetermined period after startup of the engine 10.

Furthermore, the control unit executes a determination process of making a determination on the property of the fuel supplied to the engine 10 based on the ignition sufficiency ratio. It should be noted, however, that the control unit with which the first apparatus is equipped makes a determination on the property of fuel based on a determination index value that is obtained by subjecting the ignition sufficiency ratio to "the smoothing process".

The aforementioned "smoothing process" is a process of calculating a weighted average of an ignition sufficiency ratio obtained this time and a determination index value obtained last time. The control unit with which the first apparatus is equipped determines that the property of fuel is "heavy" when the determination index value is equal to or larger than the predetermined threshold Ch. It should be noted, however, that the degree of this "smoothing process" (i.e., "the smoothing ratio") needs to assume such a value that a correct determination is made on the property of fuel. More specifically, "the smoothing ratio" needs to be set such that it is not erroneously determined that the fuel is "heavy" and it is correctly determined that the heavy fuel is "heavy" at low temperatures.

Thus, as described above with reference to FIG. 5, the control unit with which the first apparatus is equipped classifies the period after startup of the engine 10 into three periods. Then, the control unit sets "the smoothing ratio" in accordance with each of the periods. More specifically, as described above with reference to the formula (1), the control unit sets "the smoothing coefficient", which is the inverse of a coefficient corresponding to the weight of an ignition sufficiency ratio obtained this time in "the smoothing process", to a value corresponding to each of the three periods that will be enumerated below.

The first period is a period from startup of the engine (the engine 10) to attainment of the target rotational speed NT by the engine rotational speed NE. The second period is a period from attainment of the target rotational speed NT by the engine rotational speed NE to the lapse of the predetermined period t2. The third period is a period after the lapse of the aforementioned predetermined period t2 from attainment of the target rotational speed NT by the engine rotational speed NE.

The concrete value of "the smoothing coefficient" in each of the aforementioned three periods can be appropriately determined in accordance with, for example, the characteristics and the like of the internal combustion engine to which the method according to the invention is applied. More specifically, the concrete value of "the smoothing coefficient" can be appropriately determined based on, for example, an experiment or the like using the internal combustion engine.

As described above, the first apparatus classifies the predetermined period after startup of the internal combustion engine in accordance with the fluctuation pattern of the engine rotational speed, and calculates the determination index value by subjecting the ignition sufficiency ratio to "the smoothing process" that uses "the smoothing coefficient" corresponding to each of the periods. When the determination index value thus obtained is equal to or larger than the predetermined threshold Ch, the first apparatus determines that the property of fuel is "heavy". As a result, the possibility of an erroneous determination that the property of fuel is "heavy" despite the use of standard fuel is reduced. That is, the first apparatus can accurately determine, even at low temperatures, whether or not the fuel supplied to the internal combustion engine is heavy fuel.

Next, the second embodiment of the invention will be described. A determination apparatus according to the second embodiment of the invention (which will be referred to hereinafter simply as "the second apparatus") is different from the first apparatus only in that a first smoothing coefficient as the "smoothing coefficient" in the first period, a second smoothing coefficient as the "smoothing coefficient" in the second period, and a third smoothing coefficient as the "smoothing coefficient" in the third period satisfy a relationship: the first smoothing coefficient>the third smoothing coefficient the second smoothing coefficient.

As described previously with reference to FIG. 5, in the first period corresponding to the immediate post-startup range of the internal combustion engine, the engine rotational speed NE is not stable, and approaches the target rotational speed NT while repeatedly rising and falling. That is, in the first period, the engine rotational speed NE greatly fluctuates. In the subsequent second period corresponding to a complete explosion period of the internal combustion engine, the engine rotational speed NE converges toward the target rotational speed NT, and does not greatly fluctuate. Furthermore, in the third period corresponding to the post-startup range after the lapse of the aforementioned predetermined period t2 from attainment of the target rotational speed NT by the engine rotational speed NE, the engine rotational speed NE ought to be stable. However, the engine rotational speed NE and/or the target rotational speed NT may change due to an external factor, for example, the turning on of the air-conditioner, a shift operation by the driver of the vehicle, or the like.

In consideration of the fluctuation pattern of the engine rotational speed NE in each of the first period, the second period, and the third period as described above, the risk of an erroneous determination on the property of fuel based on an increase in the ignition sufficiency ratio resulting from fluctuations in the engine rotational speed NE is highest in the first period, and lowest in the second period. Thus, in the second apparatus, the first smoothing coefficient as "the smoothing coefficient" in the first period, the second smoothing coefficient as "the smoothing coefficient" in the second period, and the third smoothing coefficient as "the smoothing coefficient" in the third period are so set as to satisfy the relationship: the first smoothing coefficient>the third smoothing coefficient the second smoothing coefficient, as described above.

Owing to the foregoing, the second apparatus can execute "the smoothing process" corresponding more suitably to the fluctuation pattern of the engine rotational speed NE that is assumed in each of the aforementioned three periods. As a result, the possibility of an erroneous determination that the property of fuel is "heavy" despite the use of standard fuel is more reliably reduced. That is, the second apparatus can more accurately determine, even at low temperatures, whether or not the fuel supplied to the internal combustion engine is heavy fuel.

Next, the third embodiment of the invention will be described. A determination apparatus according to the third embodiment of the invention (which will be referred to hereinafter simply as "the third apparatus") is different from the first apparatus and the second apparatus only in that the control unit determines that the property of fuel is "heavy" when the engine rotational speed has not reached the target rotational speed even after the lapse of the predetermined period t1 from startup of the internal combustion engine.

As described previously, in the fuel property determination apparatus for the internal combustion engine according to the invention (the apparatus according to the invention), a period from startup of the internal combustion engine (the engine 10) to attainment of the target rotational speed NT by the engine rotational speed NE is defined as the first period. However, in certain situations, for example, the use of heavy fuel in a very cold land or the like, the engine rotational speed NE may remain below the target rotational speed NT for a long period that cannot be assumed in the case where standard fuel is used.

In a case as described above, even if the advancement correction amount of the ignition timing is small and the ignition sufficiency ratio does not reach a value equal to or larger than the threshold Ch in the aforementioned period in which "the engine rotational speed NE does not reach the target rotational speed NT", it is wrong to determine that the property of fuel is "not heavy". On the contrary, the long duration of a state where "the engine rotational speed NE does not reach the target rotational speed NT" means that the property of fuel is "heavy".

Thus, in the third apparatus, when the engine rotational speed has not reached the target rotational speed even after the lapse of the predetermined period t1 from startup of the internal combustion engine, the control unit determines that the property of fuel is "heavy". Thus, even in the case where the engine rotational speed NE has remained below the target rotational speed NT for a long period, it is possible to suitably determine whether or not the fuel supplied to the internal combustion engine is heavy fuel.

Next, the fourth embodiment of the invention will be described. A determination apparatus according to the fourth embodiment of the invention (which will be referred to hereinafter simply as "the fourth apparatus") is different from the first to third apparatuses only in that the internal combustion engine is further equipped with a coolant temperature sensor that detects a temperature of a coolant in the internal combustion engine, and that the control unit sets the third smoothing coefficient to 1 when the temperature of the coolant detected by the coolant temperature sensor is equal to or higher than a predetermined threshold TL at the time of startup of the internal combustion engine.

As described at the beginning, through the aforementioned "smoothing process", the apparatus according to the invention reduces the possibility of an erroneous determination that standard fuel is heavy fuel due to great fluctuations in the rotational speed and great fluctuations in the ignition timing correction amount in the internal combustion engine immediately after cold startup, and makes an accurate determination on the property of fuel. Accordingly, when there is no possibility of such an erroneous determination, there is no need to execute "the smoothing process". As a case where there is no possibility of such an erroneous determination, it is possible to mention, for example, a case where the temperature of the internal combustion engine at the time of startup is sufficiently high. In particular, when the third period (the post-startup range) has been reached via the aforementioned first period (the immediate post-startup range) and the aforementioned second period (the complete explosion range) in an internal combustion engine started at a sufficiently high temperature, the possibility of an erroneous determination that standard fuel is heavy fuel is extremely low. On the contrary, when "the smoothing process" is executed in the third period in this case, there is a possibility of an erroneous determination that heavy fuel is standard fuel. That is, in this case, there is no need to execute "the smoothing process".

Thus, the fourth apparatus is applied to an internal combustion engine that is further equipped with a coolant temperature sensor that detects a temperature of a coolant, and the control unit sets the third smoothing coefficient to 1 when the coolant temperature (the temperature of the coolant) detected by the coolant temperature sensor is equal to or higher than the predetermined threshold TL at the time of startup of the internal combustion engine. As described previously, "the smoothing process" in the apparatus according to the invention is a process of calculating a weighted average of an ignition sufficiency ratio obtained this time and a determination index value obtained last time. Besides, as "the smoothing coefficient" decreases, the degree of reflection of the ignition sufficiency ratio obtained this time on a newly calculated determination index value is increased. In the case where "the smoothing coefficient" is 1, as is also apparent from the foregoing formula (1), the newly calculated determination index value is equal to the ignition sufficiency ratio obtained this time. That is, in this case, "the smoothing process" is not executed.

Thus, the fourth apparatus can suitably determine whether or not the fuel supplied to the internal combustion engine is heavy fuel, while reducing the possibility of an erroneous determination that heavy fuel is standard fuel due to the execution of "the smoothing process" beyond necessity.

Next, the fifth embodiment of the invention will be described. A determination apparatus according to the fifth embodiment of the invention (which will be referred to hereinafter simply as "the fifth apparatus") is different from the first to fourth apparatuses only in that the internal combustion engine is further equipped with a fuel feed detection device that detects an operation of feeding fuel, and that the control unit nullifies a result of determination obtained by the determination process when the operation of feeding oil is detected by the fuel feed detection device, and prohibits the determination process from being executed when it is already determined that the property of the fuel supplied to the internal combustion engine is "heavy".

As described hitherto, the apparatus according to the invention suitably determines whether or not the fuel supplied to the internal combustion engine is heavy fuel, based on the correction amount of the ignition timing (more specifically, the determination index value that is obtained by subjecting the ignition sufficiency ratio to "the smoothing process") in a predetermined period after startup of the internal combustion engine. In general, the fuel supplied to the internal combustion engine is stored in a container, for example, a fuel tank or the like, and is supplied to the internal combustion engine from the container. Accordingly, the property of the fuel supplied to the internal combustion engine does not greatly change unless the composition of the fuel in the fuel tank changes due to, for example, the renewed feeding of fuel or the like.

Thus, as described above, the fifth apparatus prohibits the determination process from being newly executed when it is already determined that the property of the fuel supplied to the internal combustion engine is "heavy". More specifically, for example, when it is determined that the property of fuel is "heavy", the fifth apparatus maintains the data indicating that the currently used fuel is "heavy" (e.g., sets the "heaviness" determination flag ON as described previously). Thus, after the fifth apparatus determines that the property of fuel is "heavy", the control matching heavy fuel (e.g., air-fuel ratio control corresponding to heavy fuel by the ignition timing controller, etc.) can be executed without the need to newly execute the determination process every time the internal combustion engine is started up.

However, when fuel is newly fed to the internal combustion engine for reasons of, for example, a small remaining amount of fuel in the fuel tank with which the internal combustion engine is equipped, and the like, the property of the fuel supplied to the internal combustion engine afterward may change. In this case, when the result of determination on the property of fuel in the past is maintained as described above and the control based on the result of determination (e.g., air-fuel ratio control or the like) is executed, the actual property of fuel does not match the control. Consequently, the operability of the internal combustion engine and/or the exhaust emission properties may deteriorate.

Thus, when fuel is newly fed to the internal combustion engine, the fifth apparatus nullifies the result of determination on the property of fuel in the past. More specifically, the fifth apparatus is applied to an internal combustion engine that is further equipped with a fuel feed detection device that detects an operation of feeding fuel, and the control unit nullifies the result of determination obtained by the determination process (in the past) when the operation of feeding fuel is detected by the fuel feed detection device. Thus, it is possible to suitably determine whether or not the fuel supplied to the internal combustion engine is heavy fuel, while suppressing the frequency with which a determination is made on the property of fuel.

Incidentally, as described above, when fuel is newly fed to the internal combustion engine, the fifth apparatus nullifies the result of determination on the property of fuel in the past. However, when a change in the property of fuel without the renewed feeding of fuel is assumed due to, for example, volatilization of light components of the fuel in the fuel tank, the number of opportunities to nullify the result of determination on the property of fuel in the past may be increased. More specifically, the result of determination on the property of fuel in the past may be nullified, for example, every time the operation time of the internal combustion engine (which may be replaced by the running time or running distance of a vehicle in the case where the internal combustion engine is mounted in the vehicle) reaches a predetermined threshold.

Some embodiments of the invention with specific configurations have been described above with reference to the accompanying drawings when necessary, with a view to illustrating the invention. However, the scope of the invention should not be construed as being limited to these exemplary embodiments thereof. It goes without saying that the invention can be subjected to appropriate modifications within the scope set forth in the claims and the specification.

What is claimed is:

1. A fuel property determination apparatus for an internal combustion engine including an ignition plug having a spark generation portion, the fuel property determination apparatus comprising:
   an electronic control unit programmed to:
   (i) correct an ignition timing as a timing for generating a spark from the spark generation portion,
   (ii) execute feedback control of an engine rotational speed such that an engine rotational speed converges to a target rotational speed,
   (iii) calculate an ignition sufficiency ratio during a preset period after startup of the internal combustion engine, and execute a determination process of making a determination on a property of a fuel supplied to the internal combustion engine based on the ignition sufficiency ratio, the ignition sufficiency ratio being a ratio of an advancement correction amount of the ignition timing to a maximum ignition correction width as a maximum width that allows the ignition timing to be corrected when the ignition timing is corrected in the feedback control,
   (iv) determine that the property of the fuel is heavy when a determination index value obtained by subjecting the ignition sufficiency ratio to a smoothing process is equal to or larger than a predetermined threshold, the smoothing process being a process of calculating a weighted average of an ignition sufficiency ratio obtained this time and a determination index value obtained last time, and
   (v) set a smoothing coefficient to a value corresponding to each of a first period, a second period, and a third period, the smoothing coefficient being an inverse of a coefficient corresponding to a weight of the ignition sufficiency ratio obtained this time in the smoothing process, the first period being a period from startup of the internal combustion engine to attainment of the target rotational speed by the engine rotational speed, the second period being a period from attainment of the target rotational speed by the engine rotational speed to lapse of a predetermined period, and the third period being a period after lapse of the predetermined period from attainment of the target rotational speed by the engine rotational speed.

2. The fuel property determination apparatus according to claim 1, wherein
   a first smoothing coefficient is larger than a third smoothing coefficient,
   the third smoothing coefficient is larger than or equal to a second smoothing coefficient,
   the first smoothing coefficient is a smoothing coefficient in the first period,
   the second smoothing coefficient is a smoothing coefficient in the second period, and the third smoothing coefficient is a smoothing coefficient in the third period.

3. The fuel property determination apparatus according to claim 1, wherein the electronic control unit is further programmed to determine that the property of the fuel is heavy when the engine rotational speed has not reached the target rotational speed even after lapse of a predetermined period from startup of the internal combustion engine.

4. The fuel property determination apparatus according to claim 2, further comprising:
   a coolant temperature sensor configured to detect a temperature of a coolant in the internal combustion engine,
   wherein the electronic control unit is further programmed to set the third smoothing coefficient to 1 when the temperature of the coolant detected by the coolant temperature sensor at a time of startup of the internal combustion engine is equal to or higher than a predetermined threshold.

5. The fuel property determination apparatus according to claim 1, further comprising:
   a fuel feed detector configured to detect an operation of feeding fuel,
   wherein the electronic control unit is further programmed to, when the fuel feed detector detects the operation of feeding fuel, (i) nullify a result of determination obtained by the determination process, and (ii) prohibit the determination process from being executed when the electronic control unit has determined that the property of the fuel supplied to the internal combustion engine is heavy.

* * * * *